United States Patent [19]

Cook

[11] Patent Number: 5,567,438
[45] Date of Patent: Oct. 22, 1996

[54] SHELLAC DISPERSIONS AND COATINGS, AND METHOD OF FORMING AQUEOUS-BASED SHELLAC DISPERSIONS AND COATINGS

[75] Inventor: Richard B. Cook, Chelmsford, Mass.

[73] Assignee: Opta Food Ingredients, Inc., Bedford, Mass.

[21] Appl. No.: 541,227

[22] Filed: Oct. 12, 1995

Related U.S. Application Data

[63] Continuation of Ser. No. 92,386, Jul. 14, 1993, abandoned.

[51] Int. Cl.$^6$ ........................................... A61K 9/28
[52] U.S. Cl. .................... 424/474; 424/475; 424/480; 424/489; 530/201
[58] Field of Search ................................ 424/474, 475, 424/480, 489; 530/201

[56] References Cited

U.S. PATENT DOCUMENTS

| | | | |
|---|---|---|---|
| 3,390,049 | 6/1968 | Rednick et al. | |
| 4,177,177 | 12/1979 | Vanderhoff et al. | |
| 4,180,559 | 12/1979 | Huber | 424/480 |
| 4,330,338 | 5/1982 | Banker | 424/480 |
| 4,385,078 | 5/1983 | Onda et al. | 424/480 |
| 4,513,019 | 4/1985 | Brancq et al. | 424/35 |
| 5,059,248 | 10/1991 | Signorino et al. | 106/402 |
| 5,202,137 | 4/1993 | Duffy et al. | |
| 5,324,351 | 6/1994 | Oshlack et al. | 530/373 |

FOREIGN PATENT DOCUMENTS

| | | |
|---|---|---|
| 1427262 | 1/1965 | France . |
| 1467441 | 9/1963 | Germany . |
| 887682 | 1/1962 | United Kingdom . |

OTHER PUBLICATIONS

Hagenmaier, R. D., and Shaw, P. E., "Permeability of Shellac Coatings to Gases and Water Vapor," *J. Agricultural and Food Chemistry.*, 39(5):825–829 (1991).

Banker, G. S., and Peck, G. E., "The new, water-based colloidal dispersions," Pharmaceutical Technology, pp. 55–60 (1981, Apr.).

Chang, R. K., et al., "Preparation and evaluation of shellac pseudolatex as an aqueous enteric coating system for pellets," Int'l J. of Pharmaceutics, 60:171–173 (1990).

*Primary Examiner*—Nathan M. Nutter
*Assistant Examiner*—John M. Cooney, Jr.
*Attorney, Agent, or Firm*—Hamilton, Brook, Smith & Reynolds, P.C.

[57] ABSTRACT

A method of forming the aqueous-based shellac dispersion includes dissolving a shellac solution in a basic aqueous solvent to form a shellac solution and subsequently combining the shellac solution with an acidic aqueous solution, whereby the shellac precipitates to form the aqueous-based shellac dispersion. A film can be formed by applying the shellac dispersion to a suitable surface and exposing the dispersion to conditions which cause a substantial portion of the shellac particles in the dispersion to fuse, thereby forming a shellac film on the surface. The shellac film does not include any organic solvent for the shellac or any amine-containing shellac salt. A plasticizer can be employed to form a continuous shellac coating on a substrate at significantly reduced temperatures.

9 Claims, 1 Drawing Sheet

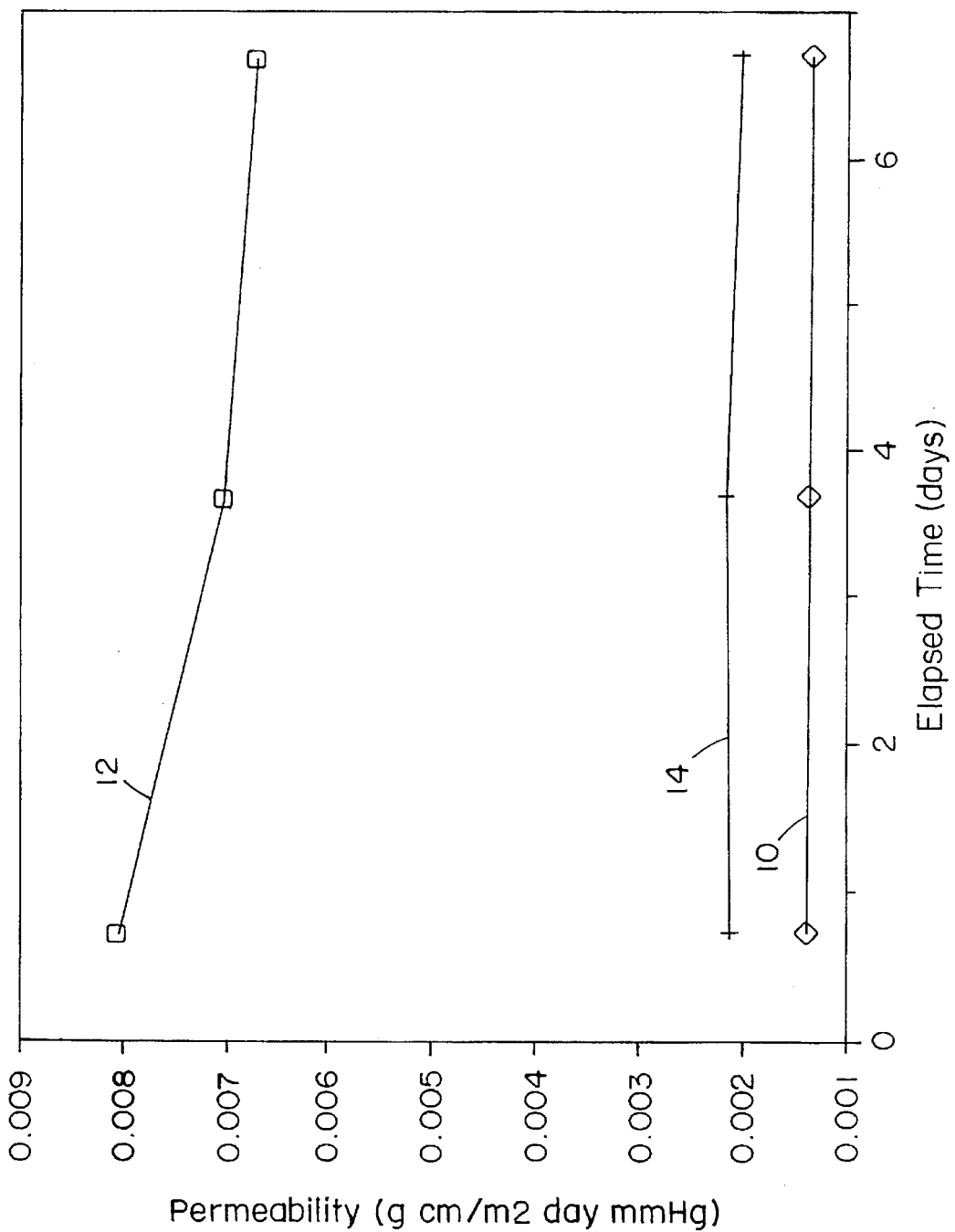

SHELLAC DISPERSIONS AND COATINGS, AND METHOD OF FORMING AQUEOUS-BASED SHELLAC DISPERSIONS AND COATINGS

This application is a continuation of application Ser. No. 08/092,386, filed on Jul. 14, 1993, now abandoned, which is incorporated herein by reference in its entirety.

BACKGROUND OF THE INVENTION

Shellac is a well-known commercial resin which originates as a secretion of an insect, *Laccifer lacca* or *Tachardia lacca*, found in Eastern countries, such as India, Pakistan and Sri Lanka. Principal components of shellac include aleuritic acid, shellolic acid and jalaric acid. Under some conditions, shellac can polymerize. However, shellac is not generally considered to be a polymer.

Shellac has been used as a coating on some foods and medications in order to improve their appearance. Examples of foods on which shellac has been applied include apples and confections. Forms of medications on which shellac has been employed as a coating include pills and tablets.

Although shellac coatings are enteric and non-toxic, shellac exhibits physical properties which make formation of such coatings problematic. For example, shellac is not water-soluble and has a melting point in the range of between about 75° and 80° C. Therefore, in order to minimize damage to surfaces to which it is applied, shellac typically must be dissolved in a medium before it is applied to a surface. The solvent can then be evaporated to leave a shellac coating.

A common method of forming shellac coatings on perishable foods and medications includes dissolving shellac in an alcohol solvent. Examples of typical solvents include denatured ethanol. However, federal regulatory requirements limit the use of ethanol. Further, explosion-proof equipment is typically required when handling alcohol-based solutions. Also, organic solvent-based solutions, such as alcohol-based solutions, typically have a residual amount of solvent in the coating. In addition, shellac components of alcohol-based coatings can polymerize over time, thereby diminishing their ability to dissolve in the digestive track and consequently reducing their value as enteric coatings.

Another method of forming a shellac coating includes dissolving shellac in an aqueous-based ammonia solution. However, subsequent volatilization of ammonia from the solution to form a shellac coating, generates toxic vapors. Further, the viscosity of aqueous-based ammonia solutions with shellac increases significantly over a period of about three to four months. These solutions generally solidify after about six months, thereby significantly limiting their shelf-life. Also, coatings which have been formed from such solutions typically include amine-containing shellac salts and are generally not resistant to water, usually dissolving or forming opaque/white blemishes when the coatings are exposed to water. Further, such coatings have an adverse taste and are susceptible to microbial contamination.

In addition, current confectionery practice requires that a priming layer of gum arabic, or an equivalent material, be applied before coating with shellac. Similarly, the alkaline, water-based shellac solutions cannot be applied directly to chocolate to produce a continuous, acceptable film.

Therefore, a need exists for an improved coating and an improved method of coating articles, such as foods and medications, which overcome the above-mentioned problems.

BRIEF DESCRIPTION OF THE DRAWING

The Figure is a plot of the moisture vapor permeability of the film coating of the invention as compared to conventional alcohol-based film coatings.

SUMMARY OF INVENTION

The present invention relates to a method of forming an aqueous-based shellac dispersion, a method of forming a shellac film, an aqueous-based shellac dispersion, and to coated substrates having a shellac film formed therefrom.

The method of forming the shellac dispersion includes dissolving a shellac in a basic aqueous solvent to form a shellac solution. The shellac solution is then combined with an acidic aqueous solution, whereby the shellac precipitates to form the aqueous-based shellac dispersion.

The method of forming a shellac film includes dissolving a shellac in a basic aqueous solvent to form a shellac solution. The shellac solution is combined with an acidic aqueous solution, whereby the shellac precipitates to form shellac particles of an aqueous-based shellac dispersion. The aqueous-based shellac dispersion is concentrated in an amount sufficient to cause the shellac particles to fuse upon application of the dispersion onto a substrate and subsequent volatilization of the aqueous medium of the dispersion. The dispersion is applied to a substrate and the aqueous medium of the dispersion is volatilized, whereby a substantial portion of the dispersed shellac particles fuse, thereby forming the shellac film on the substrate.

The shellac dispersion includes an aqueous medium and a plurality of dispersed shellac particles in the aqueous medium. A plasticizer is present in the aqueous medium in an amount sufficient to cause at least a substantial portion of the shellac particles of the dispersion to fuse upon application of the dispersion onto a substrate and subsequent volatilization of the aqueous medium.

The coated substrate includes a substrate and a film coating on the substrate. The film coating includes a continuous shellac component and a plasticizer component, but does not include any organic solvent for the shellac or any amine-containing shellac salt.

Advantages of the present invention include absence of the use of alcohol to dissolve shellac. The shellac dispersion can be stored over long periods of time without substantial viscosity increases. Also, the dispersion is not readily susceptible to microbial contamination. The dispersion can also be lyophilized for extended storage and subsequently resuspended prior to use. Also, because the shellac is in the form of a dispersion, the concentration can be modified by filtration and the shellac can be plasticized to tailor the dispersion for specific applications. The dispersion is also of milky white appearance, which is aesthetically more appealing than the brown appearance of aqueous-based ammonia solutions of shellac. Further, dispersed shellac particles in a dispersion can be fused at a moderate temperature in a range of between about, for example, 25° and 50° C., to form a glossy coating. The resulting coating is resistant to water and does not exhibit an adverse taste because there is no residual organic solvent for the shellac or any amine-containing shellac salt, as are found in known shellac coatings. With addition of an appropriate plasticizer, the shellac fusion temperature, or melting point, can be lowered to about 25°

C., thereby significantly reducing damage to substrates, such as fruits, vegetables and confections.

DETAILED DESCRIPTION OF THE INVENTION

The features and other details of the method of the invention are now particularly described with reference to the accompanying drawings and are pointed out in the claims. It will be understood that the particular embodiments of the invention are shown by the way of illustration and not as limitations of the invention. The principle features of this invention can be employed in various embodiments without departing from the scope of the invention.

The present invention includes a method of forming a shellac dispersion. The invention also includes a method of forming a film from the aqueous-based shellac dispersion, and a shellac film formed by the method.

Shellac is derived from hardened secretions of an insect, *Laccifer lacca*, more commonly known as the Lac insect. Although the chemical nature of shellac is not completely understood, it is known that it is an esterified resin formed from hydroxy fatty and sesquiterpene acids. Among the acids which have been isolated from refined shellac are aleuritic acid, shellolic acid, jalaric acid and other aliphatic acids. Other components include wax and erythrolaccin.

The method of forming an aqueous-based shellac dispersion includes dissolving shellac in a basic aqueous solvent to form a shellac solution. The shellac solution is then combined with an acidic aqueous solution, whereby the shellac precipitates to form the aqueous-based shellac dispersion.

In one embodiment of the method, about 100 grams of a suitable shellac, such as R-49 shellac, commercially available from Mantrose-Haeuser Company, is ground into a coarse powder and then dispersed in about 170 ml of 1N caustic solution. The combined powder and caustic solution are then heated to a temperature of about 80° C. to cause the shellac to dissolve in the aqueous solvent. Preferably, the pH of the resulting shellac solution is in a range of between about 7 and 7.5. Any remaining undissolved shellac is then filtered from the solution, which is then diluted with 1N caustic solution to a final volume of about 770 ml to form a basic shellac solution.

The basic shellac solution is then combined with an acidic aqueous solution. Preferably, the acidic aqueous solution is formed by combining about 100 ml of ethyl acetate with about 950 ml of water and about 50 ml of 10% acetic acid. Preferably, the acidic aqueous solution is homogenized prior to combination with the basic shellac solution. In a particularly preferred embodiment, the acidic aqueous solution is homogenized with a POLYTRON™ homogenizer, commercially available from Brinkmann Instruments, Inc., at a speed in a range of between about 5,000 and 10,000 rpm for a period of time in a range of between about one and five minutes.

Aliquots of the basic shellac solution are injected into the acidic aqueous solution, during homogenization of the acidic aqueous solution, through a bevel-tipped needle, which should be located near an inlet orifice of the homogenizer. Further, the beveled edge of the needle should be angled toward mixing blades of the homogenizer so that the basic shellac solution is injected directly into a region of relatively rapid mixing and relatively high shearing force.

The speed of the mixing blades during injection of the basic shellac solution should be at a range of between about 2,000 and 15,000 rpm. Further, the needle should have a size in the range between about eighteen and twenty-four gauge. In a particularly preferred embodiment, the needle is twenty gauge size.

An example of a suitable ratio of the amount of basic shellac solution injected into acidic aqueous solution is about 400 ml of the basic shellac solution and about 2000 ml of acidic aqueous solution. Injection of the basic shellac solution into the acidic aqueous solution under relatively rapid mixing and high shear conditions causes the shellac to precipitate as suspended particles having a diameter of about two microns, thereby forming the aqueous-based shellac dispersion.

Optionally, the shellac dispersion can be concentrated by a suitable method. In one embodiment, the shellac dispersion can be concentrated by diafiltration, using a B15 miniconcentrator, commercially available from Amicon, Inc. The final concentration of shellac in the diafiltered dispersion is about 26% by weight of the dispersion.

Alternatively, the basic shellac solution can be added to about an equal volume of acidic aqueous solution, followed by addition of a 10% acetic acid solution to adjust the final pH of the resultant dispersion to the range of between about 5.5 and 6. In a preferred embodiment, the acetic acid solution is saturated with ethyl acetate. In a particularly preferred embodiment, the ethyl acetate is substantially removed from the resulting shellac dispersion by a suitable method, such as by evaporation of the ethyl acetate and by exposing the shellac dispersion to an absolute pressure in the range of between about 175 and 275 mm Hg, and a temperature in a range of between about 35° and 45° C. until no further ethyl acetate distillate is recovered.

Preferably, residual ethyl acetate is removed from the dispersion by vacuum distillation, in order to avoid agglomeration of the dispersed shellac particles in the dispersion.

Generally, the amount of shellac solids in the dispersion will be in the range of between about 0.5 and about 15 weight percent. However, the dispersion can be concentrated by a suitable method, such as by diafiltration or through a suitable filter medium. Example of a suitable filter medium is a cellulosic-based spiral-wound cartridge, such as a S1Y type filtration cartridge, available from Amicon, Inc.

Optionally, the shellac dispersion can be lyophilized to form a powder which can be resuspended by a suitable method. In one embodiment, the shellac dispersion (~1-35%) can be lyophilized by exposure to an atmosphere having an absolute pressure in the range of between about 100 and about 400 millitorr, at a temperature in the range of between about 20° and 50° C., until the resultant powder is dry. After the shellac dispersion is lyophilized, the resulting powder can subsequently be resuspended in an aqueous medium by first, gentle mixing to wet the particles, followed by homogenizing for two minutes (at 10,000 rpm) with a polytron homogenizer.

In one embodiment of forming a shellac film by the method of invention, a Shellac dispersion, which has been formed by the method disclosed above, is applied to a suitable surface, such as that of a food article or oral medication. Examples of suitable foods include fruits, vegetables, confections, breads, cookies and cereals. Examples of suitable oral medications include tablets or capsules. The aqueous solvent of the dispersion is then allowed to evaporate by exposure, for example, to air, at a temperature in the range of between about 45° and 55° C., depending on the substrate. Evaporation of water at elevated temperatures causes the shellac particles which have been applied to a suitable surface to fuse and thereby form the shellac film.

Alternatively, the shellac particles of the dispersion can be plasticized in order to significantly lower the temperature at which the particles fuse during formation of the shellac film. Suitable plasticizers include food-grade plasticizers, such as food-grade glycols and food-grade glycerol derivatives. Examples of suitable glycols include food-grade polyethylene glycol and food-grade polypropylene glycol. Examples of suitable glycerol derivatives include: alpha and beta monoglycerides which include a fatty acid component having a carbon chain of between about two and eighteen carbon atoms; diglycerides which include a fatty acid component having a total carbon side chain length of less than about sixteen carbon atoms; triglycerides which are formed from fatty acids having carbon chains of six carbon atoms or less, such as triacetin and tributyrin; food-grade polyglycerol derivatives which have been acylated or alkylated so that their water solubility has been reduced to less than about ten percent, weight per volume, such as triglycerol trilinoleate or decaglycerol hexaoleate. Still other examples of suitable plasticizers include: 1,4 or 1,3 diols having eight or less carbon atoms, such as 2-ethyl- 1,3-hexane diol; erythritol, pentaerythritol, or sorbitol derivatives having a water solubility of less than, or equal to, ten percent, weight per volume; and esters of hydroxylated mono or dicarboxylic acids, such as ethyl lactate, triethyl citrate and diethyl tartrate.

Preferably, the amount of plasticizer is sufficient to cause the shellac particles to fuse during evaporation of the aqueous solvent at a temperature in the range of about between 20° and 30° C. during formation the shellac film. In one particularly preferred embodiment, the amount of plasticizer (propylene glycol, ethylene glycol or triacetin) is in the range between about seven and fifteen percent (preferably ~10% by weight per volume of the shellac particles).

The shellac dispersion can be applied to the substrate by a suitable method, such as by brushing or spraying the dispersion onto the substrate. Alternatively, the substrate can be immersed in the dispersion and subsequently removed from the dispersion, thereby leaving a coating of the dispersion on the substrate for subsequent formation of the shellac film. The resulting shellac coating does not include any organic solvent for the shellac and does not include any amine-containing shellac salt.

Optionally, the shellac dispersion can be mixed with an alkaline-solubilized shellac, an emulsified aqueous suspension of beeswax, an aqueous suspension of zein, or a comparable analogue, to block complete interesterification of the resulting shellac film.

The invention will now be further and specifically described by the following examples. All parts and percentages are by weight unless otherwise specified.

EXEMPLIFICATION

Example 1

Alkaline Shellac Solution Preparation

One hundred grams of Mantrose Haeuser R-49 shellac were ground in a mortar and pestle to a coarse powder, dispersed in 170 ml of 1N NaOH, and heated to ~80° C. until dissolved. The concentrated shellac solution was then diluted to 770 ml (13% solids w/v; pH ~7.5)

Example 2

Acidic Neutralization Mixture Preparation

Fifty milliliters of the shellac solution were aspirated in a 50 ml polypropylene syringe and fitted with a 21 gauge, bevel-tipped needle. The solution was then injected into a mixture of 100 ml ethyl acetate (EtOAc), 950 ml $H_2O$, and 50 ml of 10% acetic acid (HOAc) (0.5 ml of 10% HOAc were added per gram shellac). Just before injection of the aqueous shellac solution, the acidified EtOAc/$H_2O$ mixture was homogenized, using a Polytron mixer (10,000 rpm; 3 minutes). There was a slight excess of EtOAc, which resulted in the separation of a clear supernatant layer when left standing, and a slightly cloudy solution when homogenized.

Example 3

Shellac Dispersion Formation a) Method of injection: The shellac solution was injected into the acidified EtOAc/$H_2O$ "solution," below the surface and near the inlet orifice to the homogenizer. High shear and rapid mixing were also assured by placement of a homogenizer probe right next to the wall of the beaker. In addition, the beveled edge was angled toward the mixing blades of the homogenizer so that the shellac solution was injected directly into a region of maximum mixing and high shear between the beaker wall and the homogenizer probe.

b) Influence of shear/mixing and method of injection/rate: When the alkaline shellac solution was dripped dropwise onto the surface of the HOAc/EtOAc/$H_2O$ solution (Example 2), it would initially precipitate as a "pancake" and ultimately, end up as an agglomerated ball. When the alkaline shellac solution was injected into a vortex or the acidic aqueous EtOAc solution formed by a stirring bar at high speed (~500 rpm), one would, again, get only large agglomerates. By contrast, the range from ~2000 rpm to ~15,000 rpm formed stable shellac dispersions having an average particle size of about two microns.

c) A 20-gauge needle produces the least amount of non-dispersed shellac agglomerate, although both an 18-gauge and 24-gauge needle were satisfactory (using finger pressure on the syringe plunger). When a very fine needle was used, such as 30 gauge, the syringe needle plugged. On the other hand, when needle sizes larger than 18 gauge were used, the shellac almost totally agglomerated (i.e., minimal dispersion).

Example 4

Microprecipitation Stoichiometry a) Approximately 400 ml of the 13% shellac solution was microprecipitated in 5 volumes (2,000 ml) of the acidified, saturated EtOAc solution (pH ~4.5) described above. The result was ~2,400 ml of milky aqueous shellac dispersion (MASD), and only 3.23 grams (dry wt.) of agglomerate. The calculated latex concentration was ~2.1% solids (actual: 1.5% solids). The actual yield of shellac solids was 72%. This dispersion was concentrated (by diafiltration) in an Amicon B15 miniconcentrator to 26% solids.

b) A 15% shellac solution was added to an equal volume of acidified, saturated EtOAc/$H_2O$ solution, with enough 10% acetic acid addition to keep the pH between 5.5 and 6. The final microparticulated shellac solids suspension was 6.0% which could be further concentrated, after EtOAc removal, as described above. The required amount of acid required was found to be a function of the shellac acid value (i.e., amount of alkali required to solvate the shellac).

Example 5

Method of Shellac-Concentration

The residual EtOAc was removed under vacuum (~200 mm Hg) using minimal heating (i.e., <45° C.) to avoid agglomeration or film formation. Excessive heating resulted in the codistillation of water and shellac precipitated as the residual salt concentration increased. Similarly, use of either dialysis membranes or traditional diafiltration membranes (plate or spiral-wound) to concentrate the product from Example #4 above, caused EtOAc to blind the membrane. The residual EtOAc was successfully removed by low temperature (<45°) vacuum distillation.

The shellac dispersion (3% solids, 1800 ml), was then exposed to diafiltration through an EtOAc-resistant, cellulosic based spiral-wound cartridge (Amicon, type S1Y) to further concentrate the dispersion. After 65 min., 1.35 L of permeate (0.9% solids; neutralization salts) was obtained and the dispersion volume was thereby concentrated to 400 ml (@13%). It was recognized that some residual salt was contributing to the apparent solids content since complete dialysis had not been effected.

To estimate the neutralization salt concentration, an aqueous shellac dispersion (6% total solids; 36 ml volume) immediately after EtOAc removal under vacuum, was placed in a dialysis bag (5,000 MW cutoff) and dialyzed overnight against 2L of distilled water. The final volume in the bag was 41 ml. The theoretical volume-corrected concentration of solids was therefore 5.2%. The actual concentration of solids retained by the bag was 3% solids, indicating 2.2% had been lost (as salts) by dialysis. A 5 ml sample of the 3% latex (i.e., 0.15 grams shellac) was further concentrated on an Amicon B-15 concentrator to a final volume of 0.8 ml and 14%-solids content (i.e., 0 112 grams shellac). The yield of shellac, during concentration, was, therefore, ~76%.

Example 6

Demonstration of Commercial Feasibility

As a means of determining the commercial feasibility of the process, a sample of aqueous shellac intermediate was obtained from a shellac manufacturer. It was known that this intermediate was solubilized with sodium hydroxide and bleached with sodium hypochlorite. It was also known that the concentration of shellac solids was ~6% and that the residual inorganic salt was ~2%. When an attempt was made to inject this solution directly into the acidified, saturated EtOAc/$H_2O$ medium, (Example #1) a massive agglomeration of shellac resulted in virtually no desired product. Attempts at selective desalting (i.e., inorganic salt removal without shellac salt removal) were not successful with Sephadex G-10 gel permeation resin. Accordingly, the aqueous shellac intermediate was treated with 15 ml of 10% HAc for every 100 ml of shellac intermediate. The resulting shellac coagulum was then filtered and washed with four volumes of distilled water and gently pressed to fully dewater it. The concentration of anhydrous solids was then determined. A dilute solution of NaOH (0.1N) was added to the shellac coagulum, then dispersed in sufficient distilled water to become a 10% solids suspension. The suspension was heated to 50° C. with stirring and gradual NaOH addition until shellac dissolution was Complete and the pH was 7to 7.5. The solution was then diluted to 6% solids and a 60 ml aliquot was injected into 300 ml of an acidified, EtOAc saturated water mixture, as described above. The result was a milky, microparticulated suspension (~0.6%) with virtually no agglomeration. The yield of dispersed shellac was 45%. The EtOAc could be stripped under vacuum (as above) without causing agglomeration or film formation. The above procedure avoided the lengthy, problematic shellac drying process which would otherwise have to occur before the above intermediate could typically be sold.

Example 7

Evaluation of MASD Film Formation

A prototype sample of milky, aqueous shellac dispersion (MASD) at 12% solids, no EtOAc aroma i.e. Example #5, was tested against fresh samples of CRYSTALLAC™ shellac solution (~40% solids, from R-49 shellac; EtOH solvent) and SB 1/p aqueous ammoniated shellac, commercially available from Mantrose-Haeuser Company, (~25% solids, ammoniated water) were diluted to 12% solids for direct comparison with the MASD prototype. Standard operating procedure was followed in streaking form 9A Opacity-display cards (commercially available from The Leneta Co.) and drying them at different temperatures. It was found that air drying at ambient temperature resulted in only a whitish, discontinuous film coating for the MASD, while both the CRYSTALLAC™ and SB 1/p glazes dried clear and exhibited good gloss (~92.5+ and 91 respectively; glossmeter readings). When the MASD-streaked film was dried in a 58° C. oven, (having no fan for air circulation), however, a clear film was obtained which yielded gloss readings of 88.6, which was approximately the same as the other shellac coatings. When the three films were challenged with drops of water, the MASD film (dried at 50° C.) exhibited the same blush resistance as its alcohol-based counterpart (88 vs. 89). As expected, the other aqueous based shellac (SB 1/p aqueous ammoniated shellac) dissolved in water—showing no blush resistance. The MASD was, therefore, far superior to the SB 1/p aqueous ammoniated shellac in blush resistance and water barrier properties.

As can be seen in the Figure, the moisture vapor permeability of a twelve percent (w/v) MASD (Curve 10) was less than, i.e. better than, that of an alcoholic four percent (w/v) refined shellac (Curve 12) and an alcoholic twelve percent (w/v) refined shellac (Curve 14) coating. Permeability was determined by a conventional cup method (ASTM D1653-85).

Example 8

Comparison of MASD Taste Advantages

Six experienced taste panelists were each presented with four coded inverted test tubes. Each test tube was coated, on the bottom, with either a CRYSTALLAC™ solution-derived film, a SB 1/p aqueous ammoniated shellac-derived glaze, a commercial shellac-based apple wax, or Opta's MASD, all at comparable solids concentrations. The tasters were instructed to place each tube in their mouth and rub the coated surface with their tongue. They then scored each coating, relative to an uncoated test tube control, according to coating flavor intensity and quality. The average scores indicated that the MASD was far superior to the ammoniated, aqueous shellac (SB 1/p) and comparable to CRYS-TALLAC™. The MASD was also far superior to shellac-based "apple waxes" solubilized with morpholine instead of ammonia.

Example 9

Film Formation from Resuspended Shellac Particles

The process of obtaining clear shellac films from stable colloidal suspensions of shellac microparticles in water involved the fusion of the particles. To confirm this, the following experiment was performed:

1) A 2% solids suspension of MASD was frozen (−75C) and lyophilized (~100 millitorr) to produce a fine powder which was examined under scanning electron moroscopy (SEM) (26,000 x, 20 KV) and found to contain a population of individual, spheroidal microspheres having a dehydrated particle diameter of 0.1 to 0.2 microns.

2) When the lyophilized MASD was dispersed in water, it was found to form a stable suspension which could be dried at 50° C. to form a clear shellac film. Such MASD powder was convenient for adjusting the solids content of MASD suspensions for specific applications. Such powder was particularly useful in forming 20–25% solids suspensions. Such powder also provides a convenient means for storage-minimizing product volume, risk of microbial contamination, as well as maximizing shelf life.

3) When a 2% MASD suspension, as in #1 above, was dried at room temperature, an SEM of the dried film (25,000 x, 20 KV) revealed some fusion between adjacent particles. That is, the spheroidal shape of some particles was substantially distorted or lost during partial particle fusion. On a macro-scale, the air-dried film had a white, chalky appearance, resulting, in part, from the irregularity of the surface and its effect on light diffraction.

4) When the MASD suspension dried at 40+° C., complete shellac microparticle fusion occurred and a clear film resulted. No evidence of individual microparticles remained visible in the dried film.

Example 10

Plasticizing MASD Films and Dispersions

1) Propylene glycol 3–15% (based on shellac solids) in combination with MASD at 10–15% (w/v) solids produced clear blush-resistant films at 25° C. Triacetin, under comparable conditions, with 0.1–0.3% (w/v) of glycerol monolaurate also met the above criteria. It was found that low molecular weight polyethylene glycols (~400–1000 mw) could also be added at comparable ratios or admixed with propylene glycol in ratios approaching 1:1.

2) Lower concentrations of plasticizers, than indicated above, resulted in slightly cloudy or whitish films.

3) A 0.5 ml amount of each sample was deposited on a sheet of mylar plastic and then streaked with the edge of a microscope slide. The alcohol-based fast drying, CRYS-TALLAC™ shellac solution-derived film, applied in this manner, dried in ~4 min. whereas the MASD counterpart required ~6 minutes.

Example 11

MASD Coating Test on Apples a) An aqueous MASD suspension (12% (w/v) solids) was plasticized with 7% (based on shellac solids) propylene glycol and 0.1% (w/v) glyceryl monolaurate. A commercial aqueous apple "wax" solution (CAAWS) was obtained which was known to contain shellac (20%) which had been solubilized with morpholine. The CAAWS was diluted to 12% solids before testing.

b) Uncoated, U.S. Fancy Red Delicious apples were divided into two sets. One set was brush-coated with three coats of MASD, each coat followed by a 10–15 minute drying interval. The second set was treated with CAAWS in the same way. After coating was complete, the apples were allowed to cure for 1.5 hours (at 25° C. and ~55% RH) before water-blush testing.

c) The two sets of apples were then placed in water baths maintained at 35°–40° C. After 10 minutes, a whitish water blush was observed on the CAAWS apples but not on the MASD apples.

Example 12

MASD Coating Test on Chocolate

A bar of GHIRADELLI™ Chocolate was brush-coated with the MASD formulation described in Example 7, above. Spreading of the shellac on the surface of the chocolate was facilitated by addition of 0.5% (w/v) glyceryl monolaurate. After drying, it was found to have a shiny, continuous coating. In contrast, the alcohol-based shellac formed a discontinuous coating and created irregularities in the chocolate surface.

Example 13

MASD Coating Test in Sugar Wafer

1) Sugar wafers, coated with low-fat icing, deformed as water was absorbed from the icing layer into the wafer.

2) Precoating preheated (350° F.) wafers with ammonia solubilized, aqueous shellac(s) resulted in deformation of the type produced by the low-fat icing. In addition, the wafer had an objectionable off-taste resulting from residual, ammoniated shellac.

3) When a 10% solids MASD suspension, as described in Example 9, above, was applied to a preheated sugar wafer (350° F.; simulating removal from the baking oven). It was found to form a film which did not produce the unwanted deformation above. Indeed, only if the film (and wafer) were dried (hot air gun) excessively was reverse deformation observed (i.e., curling in the direction of the coated surface).

4) A second application of ~2 ml of the above suspension to a ~12×15 cm sugar wafer was followed by hot air drying until "reverse curling" began to occur. The drying was then discontinued and the wafer allowed to cool before conducting the following experiment:

a) two strips of fast-flow Whatman 41 filter paper (1.5×4 inches) were soaked, briefly, in 40% sucrose solution and allowed to air dry until slightly damp (i.e., simulating the low-fat icing level of water activity);

b) the sucrose-impregnated filter paper strips were then weighed along with control and test-coated sections of sugar wafer (~2×5 inches) and cellophane (~3×6 inches); and c) the sugar wafer sections were placed in a counter so that the side normally in contact with the icing was facing up (i.e., coated side of test section). The weighed strips of filter paper were then placed on the sugar wafer sections and covered with the weighed sections of cellophane.

Within minutes, the control sugar wafer began to bow upwards (i.e., become convex) due to moisture absorption; while no change was noted in the test coated wafer. After 10 minutes, the wafers, filter papers, and cellophane strips were reweighed.

The MASD-coated sugar wafer absorbed only 20 mg. of moisture, whereas the uncoated sugar wafer absorbed 70 mg. of water and was substantially curled. The filter paper on the coated sugar wafer lost only 50 mg. (moisture) while the control filter paper lost 80 mg. The test cellophane gained 20 mg. while the control cellophane gained 10 mg. It was recognized that some moisture would be lost due to evaporation despite the cellophane cover.

The results indicated that a water barrier coating had been conveniently created on the sugar wafer which would retard moisture migration from adjacent regions having higher moisture activity. Such functionality should have numerous applications in the maintenance or improvement of food quality.

No taste was imparted to the sugar wafer by the MASD coating. When intentionally bent or even broken, however, it was noted that the coating strengthened the wafer.

Example 14

Shellac composition film Preparation a) Standard solubility tests indicated that shellac only dissolved in very high titer alcohol (>95%) or in water, if solubilized (to pH ~7–8) with a suitable alkali. In contrast, zein only dissolved in intermediate titers of alcohol (65–90%) or in very alkaline water (>pH 10.5). Accordingly, it was not possible to combine solutions of zein and shellac for the purpose of producing composite coatings. Such coatings provided a means of preventing the gradual time-temperature dependent insolubilization of shellac films which were intended to serve as enteric coatings.

b) A MASD suspension (10% solids) was plasticized with 6% (based on MASD solids) propylene glycol and added to an aqueous dispersion of zein (10% (w/v) solids) which was also plasticized with 6% (based on zein solids) propylene glycol. The two suspensions were readily miscible. No evidence of agglomeration or precipitation of either the shellac or zein components was observed.

c) A 1 ml sample of the combined suspension was placed on a sheet of clear plastic and streaked with the edge of a microscope slide to produce a film which was allowed to air dry ~6 minutes. The resultant film was clear and blushed only slightly when challenged with a drop of water. When the type of ammonia-solubilized shellac currently used as an enteric coating was tested for water blush resistance, it was found to dissolve. The zein/shellac composite film, therefore, exhibited better water barrier properties. Since zein, as a protein, was known to form good, shelf-stable enteric coatings, its inclusion in the composite coating ensured proper disintegration of the coating in the stomach and intestine, regardless of any shellac aging.

d) An aqueous 10% MASD preparation was also found to be readily miscible with aqueous solutions of hydroxypropyl, methyl cellulose (0.5–10%) and emulsified, aqueous suspensions of beeswax.

Equivalents

Those skilled in the art will recognize, or be able to ascertain using no more than routine experimentation, many equivalents to the specific embodiments of the invention specifically described herein. Such equivalents are intended to be encompassed in the scope of claims.

I claim:

1. A shellac colloidal dispersion suitable for use in foods or medicaments, comprising:
   a) an aqueous medium that does not contain alcohol;
   b) a plurality of shellac microparticles stably dispersed in the aqueous medium, said microparticles being derived from shellac which is first solubilized in a basic aqueous medium that does not contain alcohol and then precipitated to form the shellac microparticles; and
   c) a plasticizer, present in the aqueous medium in an amount sufficient to cause at least a substantial portion of the shellac microparticles of the dispersion to fuse upon application of the dispersion onto a substrate and subsequent volatilization of the aqueous medium.

2. A shellac dispersion of claim 1, wherein concentration of the dispersed shellac microparticle is in the range of between about 1% and 35%, by weight of the dispersion.

3. A shellac dispersion of claim 2, wherein the concentration of the dispersed shellac microparticles is in the range of between about 20% and 30%, by weight of the dispersion.

4. A shellac dispersion of claim 3 wherein the amount of plasticizer present is in the range of between about 0.25% and 20%, by weight of the dispersed shellac particles.

5. A shellac dispersion of claim 4 wherein the plasticizer includes a glycol.

6. A shellac dispersion of claim 5 wherein the glycol includes propylene glycol.

7. A shellac dispersion of claim 6 wherein the glycol further includes polyethylene glycol.

8. A shellac dispersion of claim 7 wherein the ratio of propylene glycol to polyethylene glycol is about 1:1, by volume of the dispersion.

9. A shellac dispersion of claim 4 wherein the plasticizer includes glyceryl triacetate.

\* \* \* \* \*